United States Patent
Schuurkamp et al.

(10) Patent No.: US 11,547,335 B2
(45) Date of Patent: Jan. 10, 2023

(54) METHOD AND APPARATUS FOR SENDING A MESSAGE TO A SUBJECT

(71) Applicant: KONINKLIJKE PHILIPS N.V., Eindhoven (NL)

(72) Inventors: Gert-Jan Laurens Schuurkamp, Utrecht (NL); Elise Claude Valentine Talgorn, Eindhoven (NL); Isabella Hoi Kee Wong, Eindhoven (NL); Adrianus Johannes Maria Denissen, Moergestel (NL)

(73) Assignee: Koninklijke Philips N.V., Eindhoven (NL)

( * ) Notice: Subject to any disclaimer, the term of this patent is extended or adjusted under 35 U.S.C. 154(b) by 668 days.

(21) Appl. No.: 16/488,979

(22) PCT Filed: Feb. 27, 2018

(86) PCT No.: PCT/EP2018/054760
§ 371 (c)(1),
(2) Date: Aug. 27, 2019

(87) PCT Pub. No.: WO2018/158223
PCT Pub. Date: Sep. 7, 2018

(65) Prior Publication Data
US 2021/0275070 A1     Sep. 9, 2021

(30) Foreign Application Priority Data
Mar. 1, 2017   (EP) .................................. 17158706

(51) Int. Cl.
*A61B 5/16* (2006.01)
*A61B 5/11* (2006.01)
(Continued)

(52) U.S. Cl.
CPC ............ *A61B 5/165* (2013.01); *A61B 5/1118* (2013.01); *A61M 21/02* (2013.01);
(Continued)

(58) Field of Classification Search
CPC .................. A61B 5/165; A61B 5/1118; A61B 2560/0242; A61B 2562/0219;
(Continued)

(56) References Cited

U.S. PATENT DOCUMENTS

| 5,577,510 A | 11/1996 | Chittum et al. |
| 6,607,484 B2 | 8/2003 | Suzuki et al. |

(Continued)

OTHER PUBLICATIONS

International Search Report and Written Opinion in PCT/EP2018/054760 dated May 4, 2018.

*Primary Examiner* — Rex R Holmes (57) ABSTRACT

According to an aspect, there is provided a method of sending a message to a subject, the method comprising obtaining (30; 502) measurements of one or more physiological characteristics of a subject over time; determining (32; 504) a psychological state of the subject for a plurality of time periods from the measurements; and in the event that it is determined that the subject is in a psychological state of interest in a first time period, sending (34; 514) a message to the subject in a time period subsequent to the first time period in which it is determined that the subject is not in the psychological state of interest.

16 Claims, 5 Drawing Sheets

(51) Int. Cl.
*A61M 21/02* (2006.01)
*A61M 21/00* (2006.01)

(52) U.S. Cl.
CPC ............... *A61B 2560/0242* (2013.01); *A61M 2021/0044* (2013.01); *A61M 2205/3303* (2013.01)

(58) Field of Classification Search
CPC .... A61B 5/0533; A61B 5/0002; A61M 21/02; A61M 2021/0044; A61M 2205/3303
See application file for complete search history.

(56) References Cited

U.S. PATENT DOCUMENTS

| | | |
|---|---|---|
| 8,157,730 B2 | 4/2012 | Lebouf et al. |
| 8,922,376 B2 | 12/2014 | Kangas et al. |
| 9,138,186 B2 | 9/2015 | Price |
| 9,311,825 B2 | 4/2016 | Kusted et al. |
| 2008/0072691 A1 | 3/2008 | Gruber |
| 2008/0146892 A1 | 6/2008 | Leboeuf et al. |
| 2012/0289788 A1* | 11/2012 | Jain ..................... A61B 5/165 |
| | | 702/19 |
| 2014/0085101 A1 | 3/2014 | Rahman et al. |
| 2015/0297140 A1 | 10/2015 | Hernandez |
| 2016/0089038 A1* | 3/2016 | Chadderdon, III ......................... |
| | | A61B 5/02055 |
| | | 600/301 |
| 2016/0328994 A1 | 11/2016 | Nagaishi et al. |

\* cited by examiner

METHOD AND APPARATUS FOR SENDING A MESSAGE TO A SUBJECT

CROSS-REFERENCE TO PRIOR APPLICATIONS

This application is the U.S. National Phase application under 35 U.S.C. § 371 of International Application No. PCT/EP2018/054760, filed on Feb. 27, 2018, which claims the benefit of EP Patent Application No. EP 17158706.6, filed on Mar. 1, 2017. These applications are hereby incorporated by reference herein.

TECHNICAL FIELD OF THE INVENTION

This disclosure relates to methods and apparatus for sending a message to a subject.

BACKGROUND OF THE INVENTION

Applications (apps) are increasingly being used to track different aspects of our daily lives. One area of interest is apps that make people aware of their mental balance by measuring and monitoring their body, behaviour and mind data. The aim of such apps is to make people more aware of their stress levels via objective measured data (such as galvanic skin response and physical activity), as well as through the use of subjective data (such as user annotated logs of emotional state).

Such apps can track physiological characteristics such as the person's skin conductance, also known as the galvanic skin response, GSR, (i.e. sweat levels) and the person's physical activity (e.g. sitting, walking, running, cycling, in transport). The apps can also enable the person to log how they feel in daily moments (e.g. according to the type of activity that they are doing, their location and/or who they are with e.g. working at the office with colleagues, playing at home with children, cooking at home with a partner, etc).

Based on this data the user's mental balance can be calculated. The goal is to make the person more aware of moments of tension or relaxation that are experienced every day. This understanding might help the person to take control of the tense or stressed moments in a day, which might prevent repetitive short term stress moments from turning into long term stress issues.

One of the problems of determining mental balance through measures like GSR, is that although the measurements give information on the occurrence, duration and intensity of psychological states of interest (such as stressed or excited states), the underlying nature of the psychological state often cannot be determined from the data (for example, it is difficult to distinguish between the physiological readings of someone who is stressed and someone who is excited).

Therefore, to assign meaning to psychological data that is gained from physiological data, input (e.g. annotation) from the person is needed.

SUMMARY OF THE INVENTION

As described above, physiological signals (such as elevated GSR) can be caused by emotional state or by other factors such as the activity level of the subject or their environment (e.g. whether they are hot or cold). In order not to overload the subject with annotation requests (i.e. requests for the subject to indicate the reason for the elevated physiological signals), the most important signals need to be identified and annotated. In this context, this means the signals related to the subject's emotional state and not those related to other factors.

Most importantly, annotation requests, which can be in the form of push notifications from an app, requesting the subject to provide information of their emotional state should not be sent at a moment where the subject is stressed because not only receiving extra stimuli whilst stressed might further increase the subject's stress levels but also chances of reading such a message decreases drastically. Also, it is better to wait until the subject is not experiencing strong emotions before asking for their input so that they are more objective about the event and how they were feeling.

According to a first aspect there is provided a method of sending a message to a subject, the method comprising obtaining measurements of one or more physiological characteristics of a subject over time; determining a psychological state of the subject for a plurality of time periods from the measurements; and in the event that it is determined that the subject is in a psychological state of interest in a first time period, sending a message to the subject in a time period subsequent to the first time period in which it is determined that the subject is not in the psychological state of interest.

In some embodiments, the message requests the subject identify the psychological state of interest in the first time period.

In some embodiments, the time period subsequent to the first time period is the time period that immediately follows the first time period.

In alternative embodiments, the time period subsequent to the first time period is a time period that is at least a predetermined time interval after the end of the first time period.

In some embodiments, the method further comprises the step of determining values of measurements of the one or more physiological characteristics associated with a baseline psychological state; and wherein the step of determining a psychological state of the subject comprises comparing a current set of the measurements of the one or more physiological characteristics to the determined values; and determining that the subject is in a psychological state of interest if the current set of measurements of the one or more physiological characteristics deviate from the determined values.

In these embodiments, the step of determining that the subject is in a psychological state of interest can comprise determining that the subject is in a psychological state of interest if the current set of measurements deviate from the determined values by more than a predetermined amount.

In these embodiments, the step of determining that the subject is in a psychological state of interest can comprise determining that the subject is in a psychological state of interest if the current set of measurements deviate from the determined values for longer than a predetermined minimum amount of time.

In these embodiments, the baseline psychological state may not be a psychological state of interest. In these embodiments, the baseline psychological state may be a relaxed state.

In some embodiments, the method further comprises the step of obtaining measurements of one or both of the movements of the subject over time and measurements of one or more environmental parameters over time; and the step of determining a psychological state of the subject comprises determining the psychological state of the subject for the plurality of time periods from the measurements of the one or more physiological characteristics and the one or both of the measurements of the movements of the subject over time and the measurements of the one or more environmental parameters over time.

In these embodiments, the step of determining the psychological state of the subject can comprise determining that the subject is not in a psychological state of interest if the measurements of the movements of the subject over time and/or the measurements of the one or more environmental parameters over time indicate that the subject is performing a physical activity.

In these embodiments, the step of determining the psychological state of the subject comprises determining that the subject is not in a psychological state of interest if the measurements of the movements of the subject over time and/or the measurements of the one or more environmental parameters over time indicate that the subject is physically stressed due to environmental factors.

In some embodiments, the psychological state of interest is one of excited, stressed, nervous, agitated, happy and sad.

In some embodiments, the one or more physiological characteristics is one or more of heart rate, breathing rate and skin conductivity.

According to a second aspect, there is provided a computer program product comprising a computer readable medium having computer readable code embodied therein, the computer readable code being configured such that, on execution by a suitable computer or processor, the computer or processor is caused to perform any of the methods described above.

According to a third aspect, there is provided an apparatus for sending a message to a subject, the apparatus comprising a processing unit, the processing unit configured to: obtain measurements of one or more physiological characteristics of a subject over time; determine a psychological state of the subject for a plurality of time periods from the measurements; and send a message to the subject in a time period subsequent to a first time period in which it is determined that the subject is in a psychological state of interest, wherein the time period subsequent to the first time period is a time period in which it is determined that the subject is not in a psychological state of interest.

In some embodiments, the apparatus further comprises one or more physiological characteristic sensors for measuring one or more physiological characteristics of the subject.

In some embodiments, the message requests the subject identify the psychological state of interest in the first time period.

In some embodiments, the time period subsequent to the first time period is the time period that immediately follows the first time period.

In alternative embodiments, the time period subsequent to the first time period is a time period that is at least a predetermined time interval after the end of the first time period.

In some embodiments, the processing unit is further configured to determine values of measurements of the one or more physiological characteristics associated with a baseline psychological state; and wherein the processing unit is configured to determine a psychological state of the subject by comparing a current set of the measurements of the one or more physiological characteristics to the determined values; and determining that the subject is in a psychological state of interest if the current set of measurements of the one or more physiological characteristics deviate from the determined values.

In these embodiments, the processing unit can be configured to determine that the subject is in a psychological state of interest by determining that the subject is in a psychological state of interest if the current set of measurements deviate from the determined values by more than a predetermined amount.

In these embodiments, the processing unit can be configured to determine that the subject is in a psychological state of interest by determining that the subject is in a psychological state of interest if the current set of measurements deviate from the determined values for longer than a predetermined minimum amount of time.

In these embodiments, the baseline psychological state may not be a psychological state of interest. In these embodiments, the baseline psychological state may be a relaxed state.

In some embodiments, the processing unit is further configured to obtain measurements of one or both of the movements of the subject over time and measurements of one or more environmental parameters over time; and the processing unit is configured to determine a psychological state of the subject by determining the psychological state of the subject for the plurality of time periods from the measurements of the one or more physiological characteristics and the one or both of the measurements of the movements of the subject over time and the measurements of the one or more environmental parameters over time.

In these embodiments, the processing unit can be configured to determine that the subject is not in a psychological state of interest if the measurements of the movements of the subject over time and/or the measurements of the one or more environmental parameters over time indicate that the subject is performing a physical activity.

In these embodiments, the processing unit can be configured to determine that the subject is not in a psychological state of interest if the measurements of the movements of the subject over time and/or the measurements of the one or more environmental parameters over time indicate that the subject is physically stressed due to environmental factors.

In some embodiments, the apparatus further comprises a movement sensor for measuring movements of the subject over time.

In some embodiments, the apparatus further comprises an environment sensor for measuring one or more environmental parameters over time.

In some embodiments, the psychological state of interest is one of excited, stressed, nervous, agitated, happy and sad.

In some embodiments, the one or more physiological characteristics is one or more of heart rate, breathing rate and skin conductivity.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION

Figure 1:
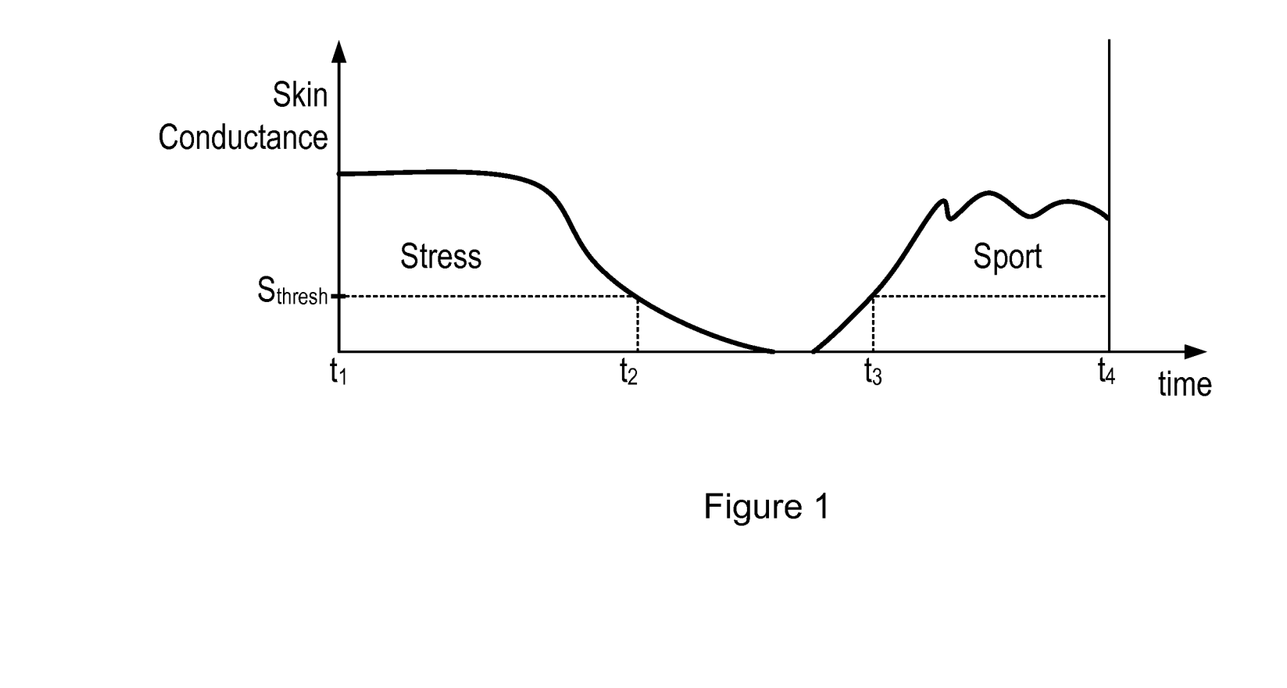
FIG. 1 is a graph showing an exemplary measurement of the skin conductance of a subject over time.

FIG. 1 is a graph showing how the skin conductance for a subject (e.g. a person) varies with time. The graph shows that the skin conductance is elevated between times $t_1$ and $t_2$ when the subject was stressed and also between $t_3$ and $t_4$ when the subject was playing sport. Between $t_2$ and $t_3$, the skin conductance is much lower, and in particular below a threshold value, $S_{thresh}$, corresponding to a period of time where the subject was feeling relaxed and was relatively sedentary.

As described above, it can be difficult to determine the causes of raised levels of physiological characteristics such as the skin conductance from the measurements alone and in many cases input from the subject is needed to correctly annotate the underlying cause of a particular feature in a physiological characteristic data set. This can be particularly relevant in the early stages of analysis where the application may be 'learning' about the subject. In applications that aim to track the subject's mood, it is particularly important to be able to distinguish between different states, for instance between whether a physiological characteristic feature is due to a physiological factor (e.g. the subject is exercising) or a psychological factor (i.e. the subject is stressed or happy). In instances where the change in the physiological characteristic is due to an emotional state, it is further desired to understand the underlying emotion that is being felt by the subject, i.e. whether the subject is happy, excited or sad.

User input is usually obtained by sending a message to the subject after a physiological characteristic is measured that might indicate an underlying psychological issue, asking the subject how they feel. Given that the aim of mood tracking applications is often to help the subject to reduce their stress levels and increase happiness, the timing of such messages is important. It might increase the subject's stress levels if, for example, every time the subject experienced stress, they received a message asking them how they were feeling. Similarly, if the subject is particularly happy or excited, then this is also an emotional state which it is undesirable to interrupt by messaging the subject. It is therefore often most appropriate to send a message when the subject seems to be in an unremarkable or 'normal' psychological state, for example, when they are relaxed or otherwise 'unemotional'. With respect to FIG. 1, it might thus be inappropriate to send a message between $t_1$ and $t_2$ when the subject is feeling stressed (i.e. the skin conductance is above the threshold $S_{thresh}$, but it might be fine to send a message with respect to the period between any time between $t_2$ and $t_4$ when the subject is not experiencing strong emotions.

Figure 2:
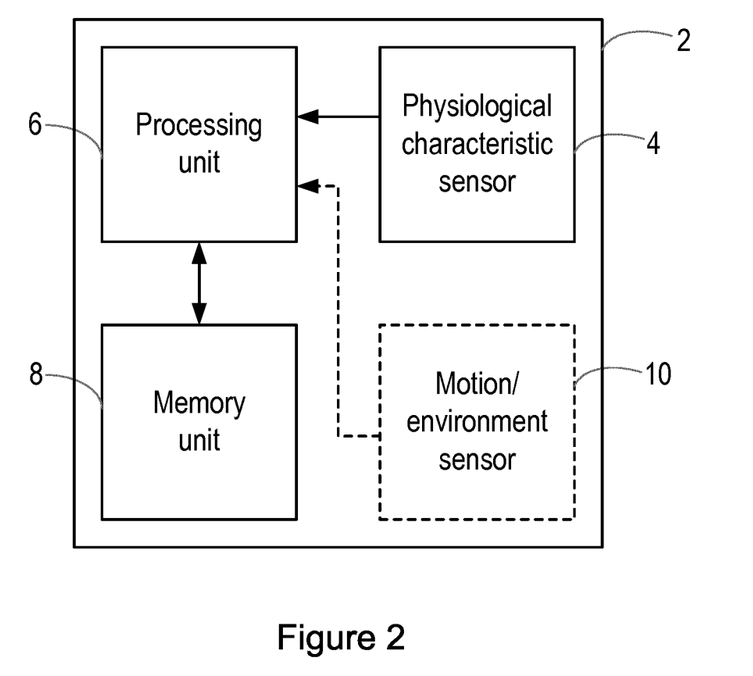
FIG. 2 is a diagram of an apparatus according to an embodiment.

FIG. 2 shows an apparatus 2 for sending a message to a subject according to an embodiment. The apparatus 2 comprises one or more physiological characteristic sensors 4 that measure one or more physiological characteristics of a subject over time and a processing unit 6. The processing unit 6 receives the measurements of the one or more physiological characteristics from the one or more physiological characteristic sensors 4 and processes the measurements to determine whether to send a message to the subject.

In some embodiments, the apparatus 2 is in a form that can be worn or carried by the subject (e.g. the apparatus 2 is portable). For example the apparatus 2 can be a smartphone, tablet or other portable electronic device. In alternative embodiments, part of the apparatus 2, (specifically the one or more physiological characteristic sensors 4), are in a form that can be worn or carried by the subject, and the other part of the apparatus 2, e.g. the part comprising the processing unit 6, is not carried or worn by the subject, for example it is in or part of an electronic device such as a laptop, desktop computer or server that can be connected to the one or more physiological characteristic sensors 4 to receive the measurements of the one or more characteristics of the subject. In some embodiments, the one or more physiological characteristic sensors 4 can be integrated into an object worn by the subject, such as a fitness tracker or mood tracker.

The processing unit 6 can receive the measurements of the one or more physiological characteristics in real-time or near real-time, and the processing unit 6 can process the measurements in real-time or near real-time, or alternatively the processing unit 6 can store the measurements for processing at a later stage (for example at the end of each hour, day, or other monitoring period), for example in memory unit 8. In addition, the processing unit 6 can control the operation of the apparatus 2, for example by activating and/or deactivating the one or more physiological characteristic sensors 4 as required.

The processing unit 6 can be implemented in numerous ways, with software and/or hardware, to perform the various functions described below. The processing unit 6 may comprise one or more microprocessors or digital signal processor (DSPs) that may be programmed using software or computer program code to perform the required functions and/or to control components of the processing unit 6 to effect the required functions. The processing unit 6 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

In various implementations, the processing unit 6 may be associated with or comprise one or more memory units 8 such as volatile and non-volatile computer memory such as RAM, PROM, EPROM, and EEPROM. The processing unit 6 or associated memory unit 8 can also be used for storing program code that can be executed by a processor in the processing unit 6 to perform the method described herein. The memory unit 8 can also be used to store signals or measurements received from the one or more physiological characteristic sensors 4. This is particularly useful where the measurements from the one or more physiological characteristic sensors 4 are stored and processed at a later stage.

The one or more physiological characteristic sensors 4 may, for example, measure one or more physiological characteristics such as skin conductance (otherwise known as the galvanic skin response), heart rate, brain signals (e.g. an electroencephalography (EEG) signal), breathing rate or blood pressure. More generally, as the skilled person will appreciate, any physiological characteristic that is influenced by the subject's psychological state may be measured by the one or more physiological characteristic sensors 4 and used by the processing unit 6 to determine whether to send a message to the subject.

Figure 3:
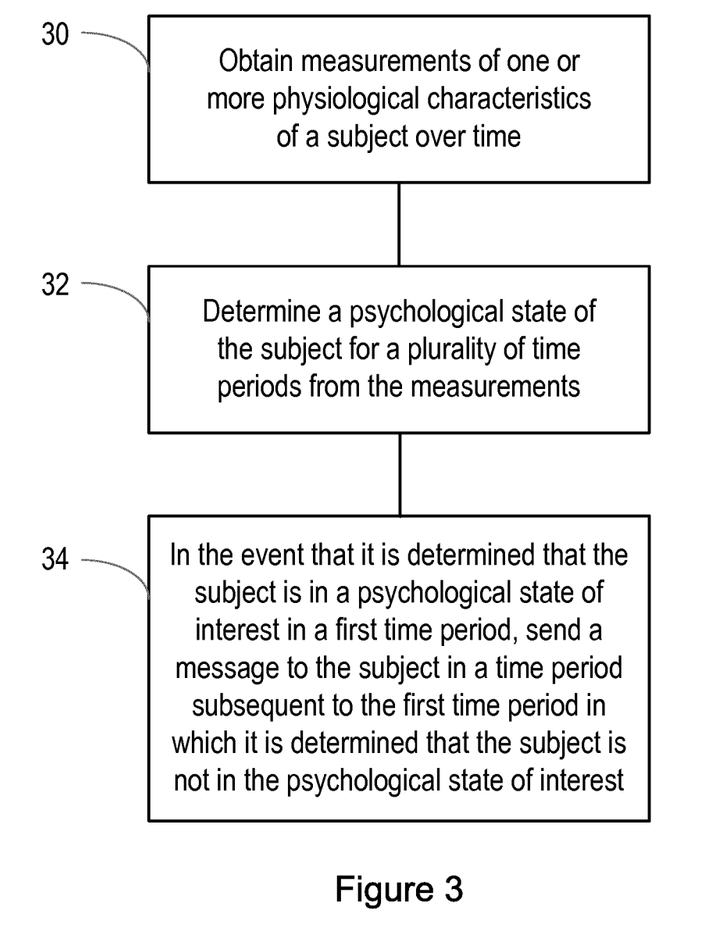
FIG. 3 is a flow chart illustrating a general method of sending a message to a subject according to an embodiment.

The flow chart in FIG. 3 shows a method of monitoring a subject according to an embodiment. The method can be performed by apparatus 2, and in particular by the processing unit 6.

In a first step 30, the processing unit 6 obtains measurements of one or more physiological characteristics of a subject over time. This step can comprise the processing unit 6 obtaining (e.g. retrieving) the measurements from a memory unit 8, receiving the measurements from a remote computer or server, or receiving the measurements directly from the one or more physiological characteristic sensors 4.

In a second step 32, the processing unit 6 determines a psychological state of the subject for a plurality of time periods from the measurements. In some embodiments, this step can comprise evaluating the measurements over a number of contiguous or overlapping time segments, for example, segments of 5 or 10 minutes in length. For some embodiments, this step may comprise evaluating the measurements over periods that are defined according to features, for example, referring to FIG. 1, $t_1$ to $t_2$ may be classed as a first time period because the skin conductance is above the threshold $S_{thresh}$ between $t_1$ and $t_2$. Similarly, $t_2$ to $t_3$ may be classified as a second time period because in this interval the skin conductance is below the threshold.

In some embodiments, a psychological state is determined with reference to a baseline measurement which represents a standard against which to judge whether the subject is experiencing strong emotions. The baseline psychological state will generally not be a psychological state for which annotation by the subject is required. As such, therefore, a baseline state may be a relaxed, unemotional, or otherwise 'normal' state where the subject is not experiencing particularly remarkable emotions, and the physiological characteristics of the subject are in a 'normal' range.

The baseline can be calculated statistically, based on typical physiological characteristic values experienced by a population of test subjects. Alternatively, the baseline can be calculated individually based on the physiological characteristics of each subject. Therefore, in some embodiments, the method comprises determining values of measurements of the one or more physiological characteristics associated with a baseline psychological state. The determined values may be in the form of a range within which measured values can be considered to be within a tolerance or threshold amount of the baseline value.

Once the baseline is established, the step 32 of determining a psychological state of the subject can comprise identifying time periods in which the physiological characteristic measurements deviate significantly (e.g. more than a threshold amount) from the baseline values. These states will be ones where the subject is likely to be experiencing strong emotions, such as stress, excitement, agitation, nervousness, happiness or sadness and are thus states for which user input will be required in order to determine which emotion the subject is experiencing (e.g. to distinguish whether they are feeling stressed or happy). States for which annotation may be required are referred to herein as 'psychological states of interest'.

Psychological states of interest can be identified by comparing the set of measurements in each time period to the baseline values and determining if the set of measurements in the time period deviates from the baseline, or deviates from the baseline by more than a threshold amount. In this way, each time period can be classified as either 'normal' or 'baseline' (or not a 'psychological state of interest') if they are within a tolerance or threshold amount of the baseline values, or as being associated with a psychological state of interest if the values of one or more physiological characteristics deviates significantly from the baseline measurement within the time period.

In some embodiments, it can be determined that the subject is in a psychological state of interest if the measurements within the time period deviate from the baseline by more than a determined amount, for example if the measurements rise above (or conversely, fall below) a threshold. In some embodiments, more than one threshold may be used, each threshold being associated with different degrees of emotion. For example, it may be that the subject is experiencing moderate stress levels if a particular physiological characteristic rises above a first threshold, but severe stress if the same physiological characteristic rises above a second, higher, threshold.

In some embodiments, a minimum time threshold may be set such that it is determined that the subject is experiencing a psychological state of interest in a time period if the physiological characteristic measurements deviate significantly from the baseline for longer than a minimum amount of time. This is to avoid short periods (e.g. a few seconds) of abnormal values of the physiological characteristics being unnecessarily identified as psychological states of interest.

In some embodiments, the intensity of an event may be used to determine a psychological state of interest has occurred. For example, a time period may be labeled as a psychological state of interest even if the measurements of the physiological characteristic in the time period deviate from the baseline for a short duration of time, so long as the deviation is particularly significant. This might be used to identify, for example, when the person experiences shock or other, sudden, unexpected emotions.

As shown in FIG. 1, elevated levels of a physiological characteristic may occur due to factors other than psychological state, for example, due to activity level or the environment (e.g. because the subject is hot or cold). Therefore, in some embodiments, measurements of one or both of the movement of the subject and measurements of one or more environmental factors over time are obtained. Referring back to FIG. 2, such measurements may be obtained using a motion sensor and/or an environment sensor 10 in the apparatus 2. In some embodiments, information from an agenda or calendar of the subject can also or alternatively be obtained, since that could indicate that the subject is/was scheduled to go to the gym, for example, and/or information from a connected device could be obtained, e.g. from a connected bicycle, etc., showing that the subject is/was using that device.

The motion sensor 10 can obtain measurements of the motion of the subject over time. The motion sensor 10 can be, for example, an accelerometer or gyroscope. The environmental sensor 10 can obtain measurements of one or more environmental parameters. The environment sensor 10 can include, for example, a temperature sensor to record the ambient temperature at the subject's location, and/or a light sensor to detect the ambient light level.

The psychological state of the subject can then be determined from the measurements of the one or more physiological characteristics made by the one or more physiological characteristic sensors 4 in combination with the measurements of the movements of the subject over time and/or the measurements of the one or more environmental parameters over time received from the motion and/or environment sensors 10.

For example, it can be determined that the subject is not experiencing a psychological state of interest if a motion sensor 10 indicates that the subject's physiological characteristics are deviating from a baseline measurement due to the physical activity. For example, a correlation between elevated levels of skin conductance (indicating that the subject is sweating) and movement likely indicate that the subject is exercising and not experiencing a psychological state of interest.

In another embodiment, it may be determined that the subject is not experiencing a psychological state of interest if the measurements of the movements of the subject over time and/or the measurements of the one or more environmental parameters over time indicate that the subject is physically stressed due to environmental factors. For example, high levels of skin conductance (indicating that the subject is sweating) combined with a high ambient temperature or high light levels might indicate that the subject is hot, as opposed to experiencing a psychological state of interest.

Figure 4:
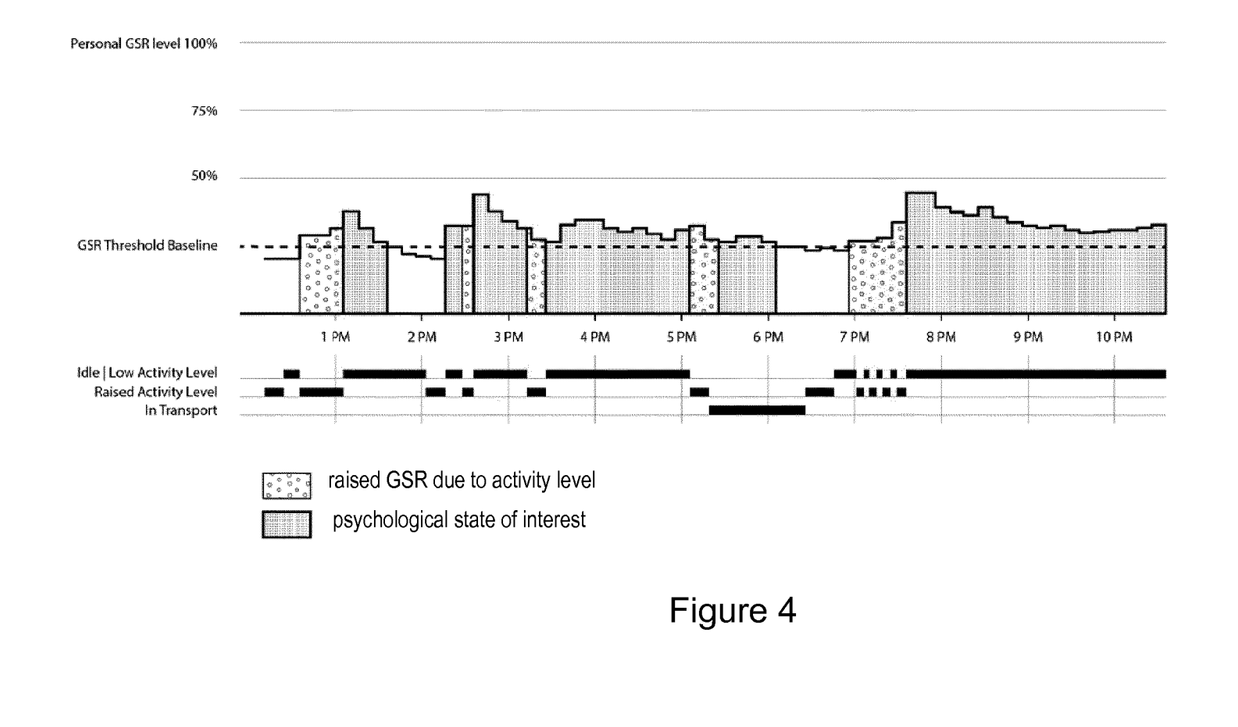
FIG. 4 is a graph showing exemplary measurements of the skin conductance, motion and skin temperature of a subject over time.

FIG. 4 shows a graph of skin conductance (GSR) over time along with an indication of the activity of the subject. In particular, FIG. 4 shows skin conductance relative to a threshold level or baseline measurement for the hours of 12 pm to 1030 pm for a subject. The indication of the activity (which could, for example, be determined from measurements from a motion sensor 10) classifies the activity of the subject at all times into one or three categories: an idle or low activity level (e.g. an activity level below a threshold), a raised activity level (e.g. an activity level above a threshold), and the subject being in transport (e.g. in a car or on a bus or train).

It can be seen in FIG. 4 that the skin conductance for the subject is above the threshold/baseline for much of the time period over which the skin conductance is measured. However, correlating the skin conductance with the determined activity level shows that several of the time periods in which the skin conductance is above the threshold corresponds to when the subject has a high/raised activity level. In this case, these time periods are not psychological states of interest. The time periods where the skin conductance is above the threshold and the activity level indicates that the subject is idle/has a low activity level or is in transport, are time periods where the psychological state of the subject is of interest.

Returning now to FIG. 3, in a step 34, in the event that it is determined that the subject is in a psychological state of interest in a particular period of the plurality of time periods, the method comprises sending a message to the subject in a subsequent time period, when the subject is no longer in a psychological state of interest.

The message can be sent in a time period immediately after the time period where the psychological state of interest occurred. For example, in embodiments where the physiological characteristics are compared to a baseline to determine the psychological state, the message can be sent as soon as it is determined that the subject is not in a psychological state of interest, i.e. as soon as the physiological characteristic has returned to within a tolerance or threshold amount of the baseline value. In the example shown in FIG. 4, a message could be sent shortly after 605 pm in respect of the time period from approximately 520 pm to 605 pm when the skin conductance was above the threshold value and the subject was in transport. Alternatively, the message can be sent a predetermined time after the psychological state of interest has ended. For example a message could be sent 30 minutes after a psychological state of interest has ended. Thus in the example shown in FIG. 4, a message could be sent around 635 pm in respect of the time period from approximately 520 pm to 605 pm in which the skin conductance was above the threshold value and the subject was in transport. As described above, it may be beneficial or desirable to leave some time between the occurrence of the psychological state of interest and the sending of the message, to ensure that subject has returned to a normal state. This also increases the chances that the subject actually reads the message.

The method may further comprise determining the subject's current psychological state immediately before sending the message, so that, for example, if the subject experiences two stressful events in a short period of time, a message isn't sent to the subject during the second stressful event asking them to identify the nature of the first event.

In some embodiments, a message can still be sent even if the physiological characteristic measurements deviate from the baseline values by more than a threshold amount if it is determined that the deviation is not due to the subject experiencing a psychological state of interest. For example, it may be acceptable to send a message to the subject if it is determined that the subject is currently exercising or is hot or cold.

In some embodiments, the processing unit 6 may be configured to include a learning element that, updates one or more of the parameters or thresholds described above in relation to the identification of the psychological states of interest, based on the annotations of previous psychological states that were provided by the subject.

As described above, in some embodiments, the message requests the subject to identify the psychological state of interest, for example, the message may ask the subject whether they were experiencing a strong emotion such as stress, happiness etc., or the message may simply ask the subject to identify the psychological state or cause of the psychological state.

The subject may input a reply to the message into the apparatus 2 or other electronic device, for example via a user interface component, such as a keyboard or touch screen. Thus, in some embodiments, the method further comprises receiving a reply to the message from the subject.

In some embodiments, the processing unit 6 may use the information on the psychological state provided by the subject in response to the message to ensure that other messages, such as motivational messages (e.g. that are used to improve the subject's psychological state) are sent at an appropriate time.

The message can be any type of electronic message, for example, the message can be a push notification for an application that is operating, running or installed on the apparatus 2 or other electronic device, such as a smartphone, or a text message sent to the subject. As is known, push notifications can be used to provide information to a subject without the subject specifically requesting the information. Thus step 34 can comprise presenting a message to the subject on the apparatus 2 or on another electronic device associated with the subject, such as a smart phone, tablet or other electronic device. For example, the message can be displayed on a screen of the apparatus 2 or other electronic device, or provided as in an audible form via a speaker of the apparatus 2 or other electronic device.

Figure 5:
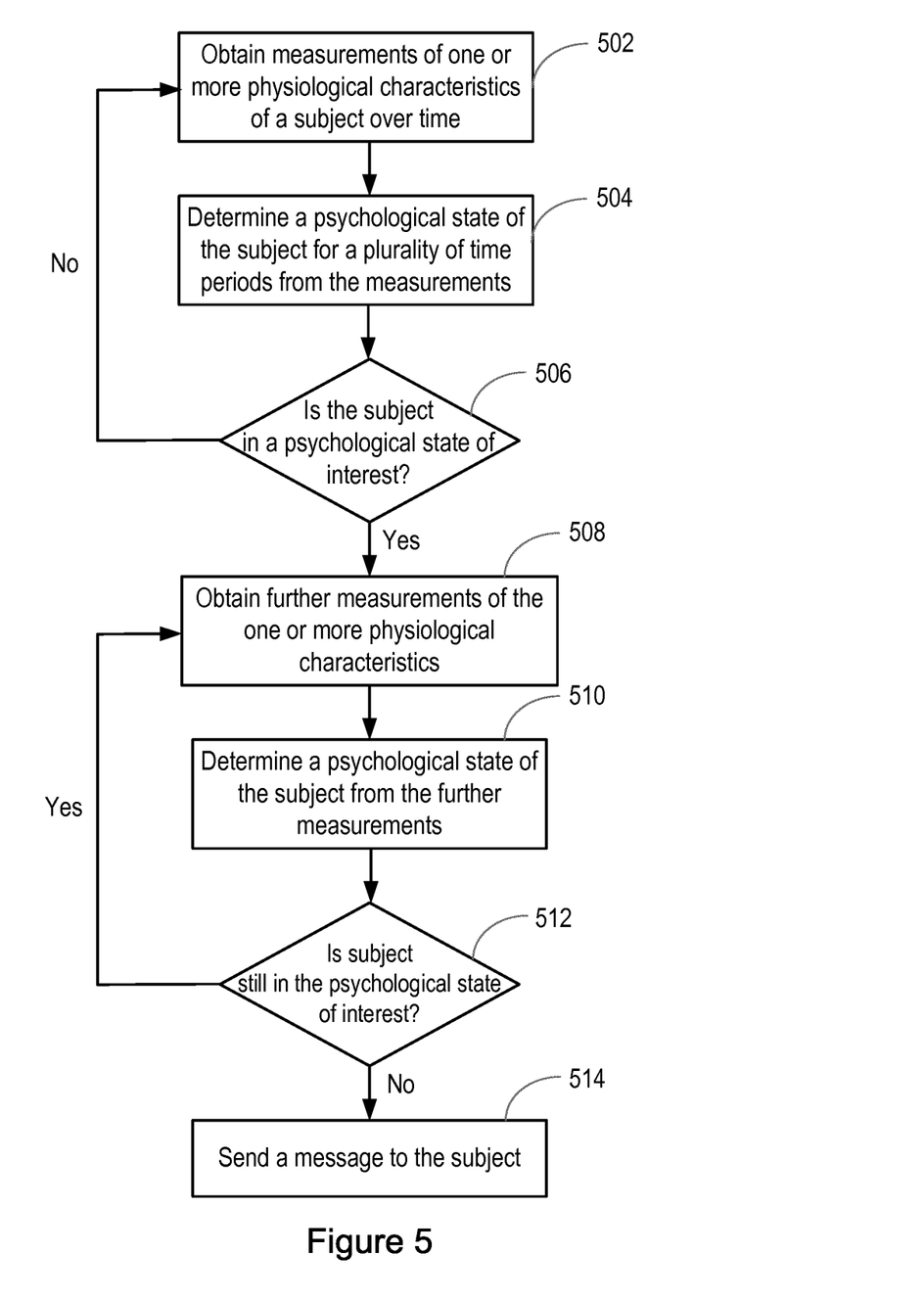
FIG. 5 is a flow chart illustrating a general method of sending a message to a subject according to a further embodiment.

FIG. 5 shows a block diagram of a method according to another embodiment of the invention. The method comprises a first step (step 502) of obtaining measurements of one or more physiological characteristics of a subject over time and a second step (step 504) of determining a psychological state of the subject for a plurality of time periods from the measurements. Steps 502 and 504 can correspond generally to steps 30 and 32 respectively of FIG. 3.

In a third step (Step 506), it is determined whether the subject is in a psychological state of interest. Step 506 can be performed using any of the methods or techniques described above. If it is determined that the subject is not in a psychological state of interest, then the method returns to step 502 and more or further physiological characteristic measurements are obtained. If it is determined that the subject is in a psychological state of interest, then it is necessary to send a message to the subject to determine the type of psychological state and/or reason for the psychological state. However, the message should not be sent until the subject is no longer in the psychological state of interest. Thus, the method moves to step 508 in which further measurements of the one or more physiological characteristics are obtained. In step 510 the psychological state of the subject is determined from the further measurements, using the same techniques as were described with respect to steps 32 and 504 above.

In step 112 if it is determined that the subject is still in the psychological state of interest (that was identified in step 506). If so, then the method returns to step 508 and further measurements of the one or more physiological characteristics are obtained. However, if at step 512 it is determined from the further measurements that the subject is no longer in the psychological state of interest, then a message relating to the psychological state of interest can be sent to the subject (step 514). Thus, as with the method in FIG. 3, a message is sent to a subject after the subject has experienced a psychological state of interest, whilst ensuring that the subject is no longer in a psychological state of interest. This reduces the risk of further stress or interruption that the subject might feel due to receipt of the message, whilst enabling the subject to provide annotation of their psychological state.

While the invention has been discussed as useful/advantageous for annotating a psychological state of a subject by determining when it is best to push a message or notification such that it does not further stress/bother the person, it can be also be used in a similar fashion to push a message intended to coach a person, such health coaching messages, when the person is no more stressed. By doing so it increases chances of actually reading the message.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of sending a message to a subject, the method comprising:
    obtaining measurements of one or more physiological characteristics of a subject,
        wherein the measurements are taken over a first plurality of time periods;
    determining a psychological state of the subject during each of the first plurality of time periods; and
    determining that the subject is in a psychological state of interest in a first time period,
    determining that the subject is not in the psychological state of interest in a second time period subsequent to the first time period, and
    automatically sending a message to the subject in the second time period,
    wherein the message requests that the subject identify an emotion state of the subject in the first time period.

2. The method as in claim 1, wherein the method further comprises:
    determining baseline values of measurements of the one or more physiological characteristics associated with a baseline psychological state,
    wherein the determining of the baseline values comprises:
    comparing a current set of the measurements of the one or more physiological characteristics to the baseline values; and
    determining that the subject is in a psychological state of interest if the current set of measurements of the one or more physiological characteristics deviate from the baseline values.

3. The method as in claim 2, comprising determining that the subject is in a psychological state of interest if the current set of measurements deviate from the baseline values by more than a predetermined amount.

4. The method as in claim 2, comprising determining that the subject is in a psychological state of interest if the current set of measurements deviate from the baseline values for longer than a predetermined minimum amount of time.

5. The method as in claim 1 further comprising:
    obtaining movement measurements of the movements of the subject over a second plurality of time periods;
    obtaining environmental measurements of one or more environmental parameters over a third plurality of time periods; and
    determining the psychological state of the subject for each of the second plurality of time periods and each of the third plurality of time periods.

6. The method as in claim 5, wherein the determining the psychological state of the subject comprises determining that the subject is not in a psychological state of interest if at least one of the movement measurements or the environmental measurements indicate that the subject is performing a physical activity.

7. The method as in claim 5, wherein the determining the psychological state of the subject comprises determining that the subject is not in a psychological state of interest if at least one of the movement measurements or the environmental measurements indicate that the subject is physically stressed due to environmental factors.

8. A non-transitory computer readable medium comprising computer readable code, wherein the computer readable code is configured such that, on execution by a suitable computer or processor, the computer or processor is caused to perform the method of claim 1.

9. An apparatus for sending a message to a subject, the apparatus comprising:
a processing circuit, the processing circuit configured to:
obtain measurements of one or more physiological characteristics of a subject,
wherein the measurements are taken over a first plurality of time periods;
determine a psychological state of the subject during each of the first plurality of time periods;
determine that the subject is in a psychological state of interest in a first time period;
determine that the subject is not in the psychological state of interest in a second time period subsequent to the first time period; and
automatically send a message to the subject in a second time period;
wherein the message requests that the subject identify an emotional state of the subject in the first time period.

10. The apparatus as in claim 9, wherein the processing circuit is further configured to:
determine baseline values of measurements of the one or more physiological characteristics associated with a baseline psychological state,
wherein the processing circuit is configured to determine a psychological state of the subject by:
comparing a current set of the measurements of the one or more physiological characteristics to the baseline values; and
determining that the subject is in a psychological state of interest if the current set of measurements of the one or more physiological characteristics deviate from the baseline values.

11. The apparatus as in claim 9, wherein the processing circuit is further configured to:
obtain movement measurements of the movements of the subject over a second plurality of time periods; and
obtaining environmental measurements of one or more environmental parameters over a third plurality of time periods,
wherein the processing circuit is configured to determine a psychological state of the subject by determining the psychological state of the subject for each of the second plurality of time periods and each of the third plurality of time periods.

12. The apparatus as in claim 11, wherein the processing circuit is configured to determine the psychological state of the subject by determining that the subject is not in a psychological state of interest if at least one of the movement measurements or the environmental measurements indicate that the subject is performing a physical activity.

13. The apparatus as in claim 9, wherein the apparatus further comprises a physiological characteristic sensor for measuring one or more physiological characteristics of the subject over time.

14. The apparatus as in claim 11, wherein the processing circuit is configured to determine the psychological state of the subject by determining that the subject is not in a psychological state of interest if at least one of the movement measurements or the environmental measurements indicate that the subject is physically stressed due to environmental factors.

15. The apparatus of claim 9, wherein the processing circuit is configured to:
store a record of the psychological state of the subject;
receive a response to the message from the subject; and
annotate the record based on the response.

16. The method of claim 1, comprising:
storing a record of the psychological state of the subject;
receiving a response to the message from the subject; and
annotating the record based on the response.

* * * * *